United States Patent [19]
Mourier

[11] 3,943,437
[45] Mar. 9, 1976

[54] APPARATUS FOR INVESTIGATING THE ELECTROSTATIC PROPERTIES OF POWDERS

[75] Inventor: Marcel Mourier, Lyon, France

[73] Assignee: Rhone-Poulenc Industries, Paris, France

[22] Filed: Jan. 20, 1975

[21] Appl. No.: 542,269

[30] Foreign Application Priority Data
Jan. 21, 1974 France .............................. 74.01915

[52] U.S. Cl. ..................................... 324/32; 324/72
[51] Int. Cl.² ..................... G01R 29/12; G01R 5/28
[58] Field of Search ..................... 324/32, 72; 307/3

[56] References Cited
UNITED STATES PATENTS
3,727,125   4/1973   Mourier ................................ 324/32

*Primary Examiner*—R. V. Rolinec
*Assistant Examiner*—Vincent J. Sunderdick
*Attorney, Agent, or Firm*—Stevens, Davis, Miller & Mosher

[57] ABSTRACT

Apparatus for measuring the electrostatic properties of materials, particularly powder, in which a first fixed plate has a series of openings lying along the circumference of the circle the center of which lies on the axis of a rotor mounted adjacent the plate with its axis perpendicular to the plate, the motor carrying an electrode and probe spaced apart from one another in such positions that the electrode and the probe separately pass over each opening when the rotor rotates. The electrode is charged and means are provided for detecting the charge on the probe to detect the charge on the material. In order to hold the powdered material in the openings a second fixed plate is mounted under the first fixed plate and has cavities therein in register with the openings in the first fixed plate, each cavity having a porous element at the bottom, and suction is applied below the porous element to hold the powder in place.

3 Claims, 5 Drawing Figures

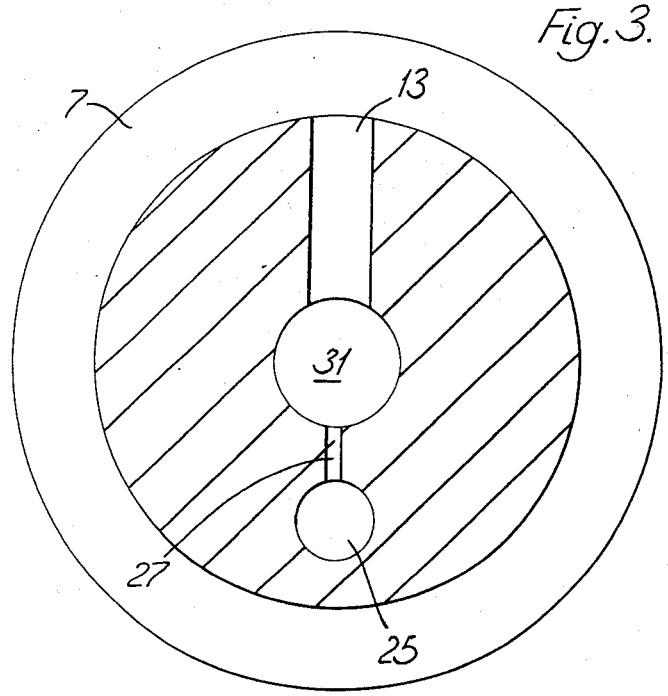
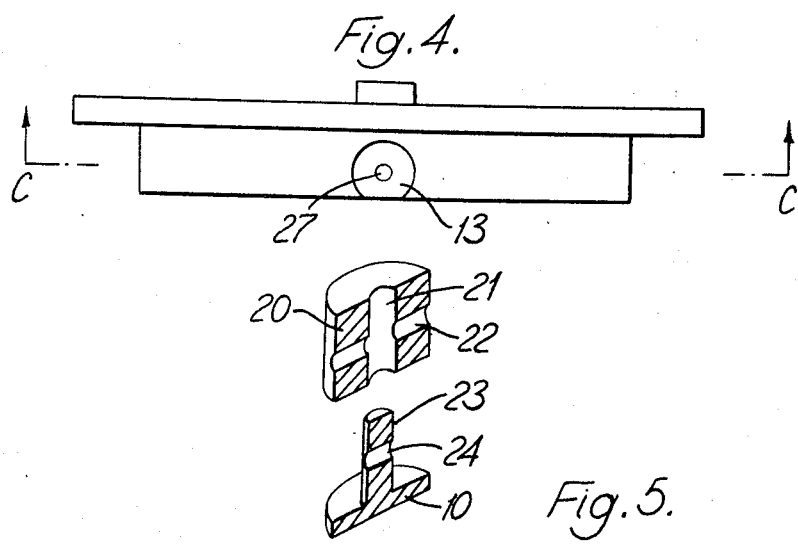

APPARATUS FOR INVESTIGATING THE ELECTROSTATIC PROPERTIES OF POWDERS

The present invention relates to apparatus for measuring the electrostatic properties of powder.

An apparatus has been described in U.S. Pat. No. 3,727,125 for investigating and measuring the electrostatic properties of materials, which can become charged and discharged at the surface, the apparatus being intended to be connected electrically to a continuous high tension current generator and to measuring components, forming a measuring head. This apparatus described includes:

a. a fixed block, made of a conducting material, carrying an earthing terminal, and having identical apertures uniformly distributed around a circle thereon;

b. an electric motor firmly fixed to the said block, the shaft of which, connected to an earthing terminal, is perpendicular to the block at the center of the circle;

c. a revolving plate fixed along its axis to the shaft of the motor, between the motor and the block;

d. a corona-effect charging electrode and a static induction measuring probe, fixed to the face of the revolving plate opposite the block, parallel to the latter and at an average distance from the axis of the plate equal to the average distance from the apertures to the centre of the circle defined above;

e. an electrical connection comprising a revolving contact which makes it possible to transmit to the charging electrode an electrical voltage with an absolute value of between 2 and 20 kV, and f. an electrical connection comprising a revolving contact which makes it possible to transmit to the measuring components the signals captured by the measuring probe.

If this apparatus is used to measure the properties of pulverulent products, the rotation at a relatively high speed of the revolving plate in the vicinity of the product investigated leads to local air movements which generally prevent the pulverulent products from remaining stable, and this applies to a greater extent, the lighter and finer are the pulverulent products. It is true that the pulverulent products can be converted to pellet form, when this is possible, but their electrostatic behavior is generally changed by so doing.

According to the present invention there is provided an apparatus for measuring the electrostatic properties of materials, such apparatus comprising a first fixed plate, a rotor mounted to rotate about an axis perpendicular to the first fixed plate, openings in the first fixed plate, openings lying along the circumference of a circle, the center of said circle lying on said axis of said rotor, an electrode and a probe fixed to said rotor and spaced apart from one another and positioned whereby both the electrode and the probe separately overlie each of said openings in turn when the rotor rotates, means for charging said electrode, means for detecting the charge on said probe, and thereby detecting the charge on said materials, a second fixed plate having means to hold it against said first fixed plate, cavities in said second fixed plate at locations overlying the openings in said first fixed plate, at least one porous element at the bottom of each said cavity and means for sucking air at the bottom of the said cavities through said porous elements.

In order that the invention may be better understood, the following description is given merely by way of example, reference being made to the accompanying drawings in which:

FIG. 3 is a view from below of the rotor of the measuring head along the section line cc of FIG. 4;

FIG. 4 is a view from the left of the rotor, positioned as in FIG. 1, of the measuring head; and FIG. 5 is a sectional perspective view of the insulating bush and the measuring probe.

Figure 1:
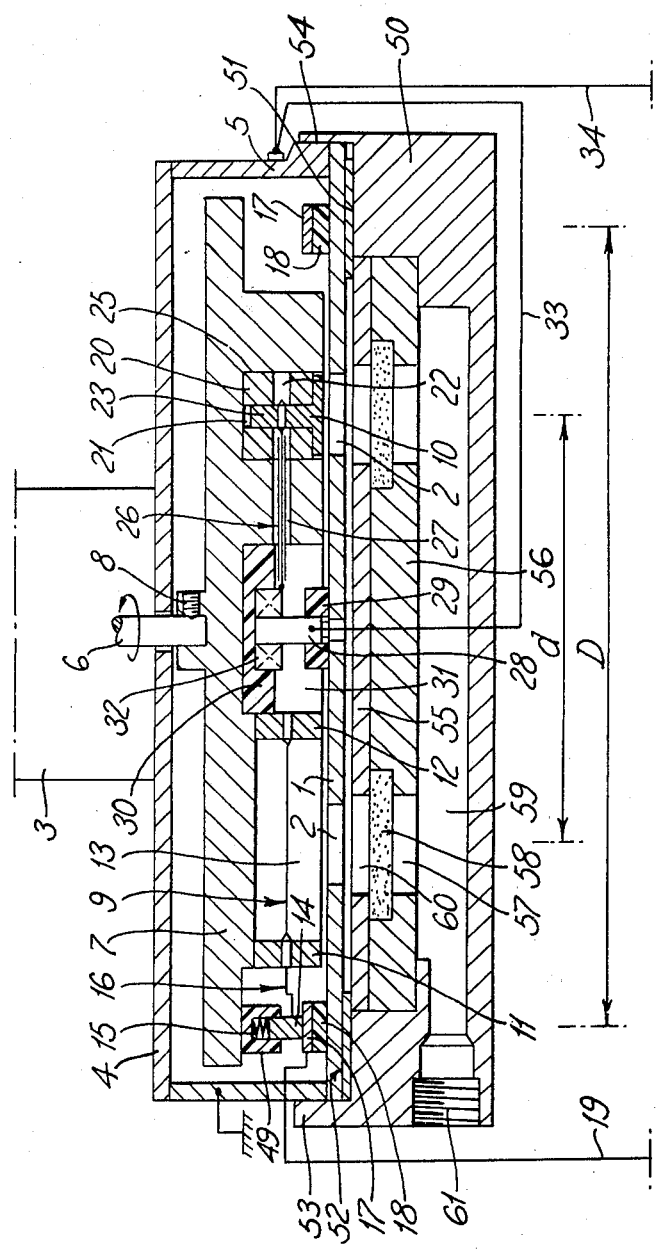
FIG. 1 is a view in section of the measuring head.

The measuring head, shown in FIG. 1, comprises a first plane fixed plate 1 of conducting material, usually metallic, carrying an earthing terminal. This plate 1 is provided with equidistant openings 2 distributed over the circumference of a circle of diameter $d$. An electric motor 3 is fixed to a support 4 connected to the plate 1 by struts 5. These struts may be extended beyond the plate 1 by insulating feet, not shown, of a height of generally less than 5 mm. The shaft 6 of the motor is connected to a lead, not shown, for earthing it, and is arranged perpendicular to the plate 1 at the center of the previously defined circumference. A circular rotor 7 is fixed to the shaft 6; advantageously, it is secured by the screw 8 and can therefore be rotated by the motor. An electrode 9, charging by corona effect, and a measuring probe 10 are arranged in the rotor 7 opposite the plate 1, parallel to the latter and at a mean distance from the axis of the rotor equal to the mean distance of the openings 2 to the center of the circumference of a circle of diameter $d$. A handle (not shown) may also be provided to facilitate manipulation of the measuring head.

The charging electrode 9, generally consisting of a radial metal wire, is held by two insulating supports 11 and 12, for example of polytetrafluorethylene mounted in a cylindrical recess 13 of the rotor 7. The charging electrode 9 is connected to a rotating contact 14 permitting its electrical connection to a high-tension D.C. generator. The rotating contact may be a carbon wiper 14 held by a spring 15 against a conducting circular track 17, for example of metal, of means diameter D. The carbon wiper 14 is connected to the electrode 9 by a sheathed wire 16. It is moved by the action of a spring 15 in the interior of a recess in insulating material 49 fixed to the rotor 7. The track 17 is fixed to the plate 1 by means of an insulating support of the same diameter. The track is connected by a flexible cable 19 permitting its electrical connection to a high-tension generator, the whole being constructed to permit raising the charging electrode to a positive or negative potential of between 2 and 20 kV.

The measuring probe 10 consists (see FIG. 5) of a metal plate of area substantially equal to that of the openings 2. It is extended by an axial shank 23 and is insulated from earth by a supporting sleeve 20, for example of polytetrafluorethylene. Preferably, the shank of the probe is provided with a passage 24 and the sleeve is cylindrical and is provided with two passages, one 21 axial, the other 22 radial. The shank 23 is forcibly inserted in the passage 21 until the passages 22 and 24 are in line with each other. The sleeve 20 is fitted in the recess 25 of the rotor (see FIG. 3).

The probe 10, fixed to the rotor 7, is connected electrically to a rotating contact permitting its connection to the measuring elements. Preferably, the rotating contact and its electrical connection are composed as follows:

The contact is formed of a ball bearing 32. The outer race of the bearing is connected to the probe 10 by a sheathed wire 26 housed in a passage 27 of the rotor 7, and in the passage 22 extending the passage 27. This race is held inside an insulating piece 30 secured to the rotor 7 inside a cylindrical recess 31. The inner race of the bearing is fitted around a fixed rod 28 held on the plate 1 by the insulating strut 29. The rod 28 is connected to the measuring elements first by a sheathed wire 33 housed in a groove of the plate 1 as far as a strut 5, then from there to an armoured cable 34 to the control box shown in FIG. 2. (For greater clarity, the wire 33 has been shown in FIGS. 1 and 2 as being outside the plate 1.).

The openings 2 of the plate are preferably so distributed that the shortest distance between two consecutive openings is substantially equal to the width of an opening. Each opening has generally a symmetrical form relative to a radial plane (for providing a symmetrical signal); the dimensions of these openings and their interspacing are predetermined for providing a substantially sinusoidal measuring signal. For facility of construction, it is preferable to use circular openings.

The probe has preferably the same shape as the openings. Preferably the openings and probes are circular and of the same diameter.

The measuring head according to the invention may, for its use, be connected to any high-tension D.C. generator, the polarity of which may be selected and which may be capable of supplying a tension between 2 and 20 kV. Generally, the charging electrode is supplied with a tension of between 3 and 10 kV. The measuring probe may be connected to any conventional apparatus capable of measuring electrical charges.

Figure 2:
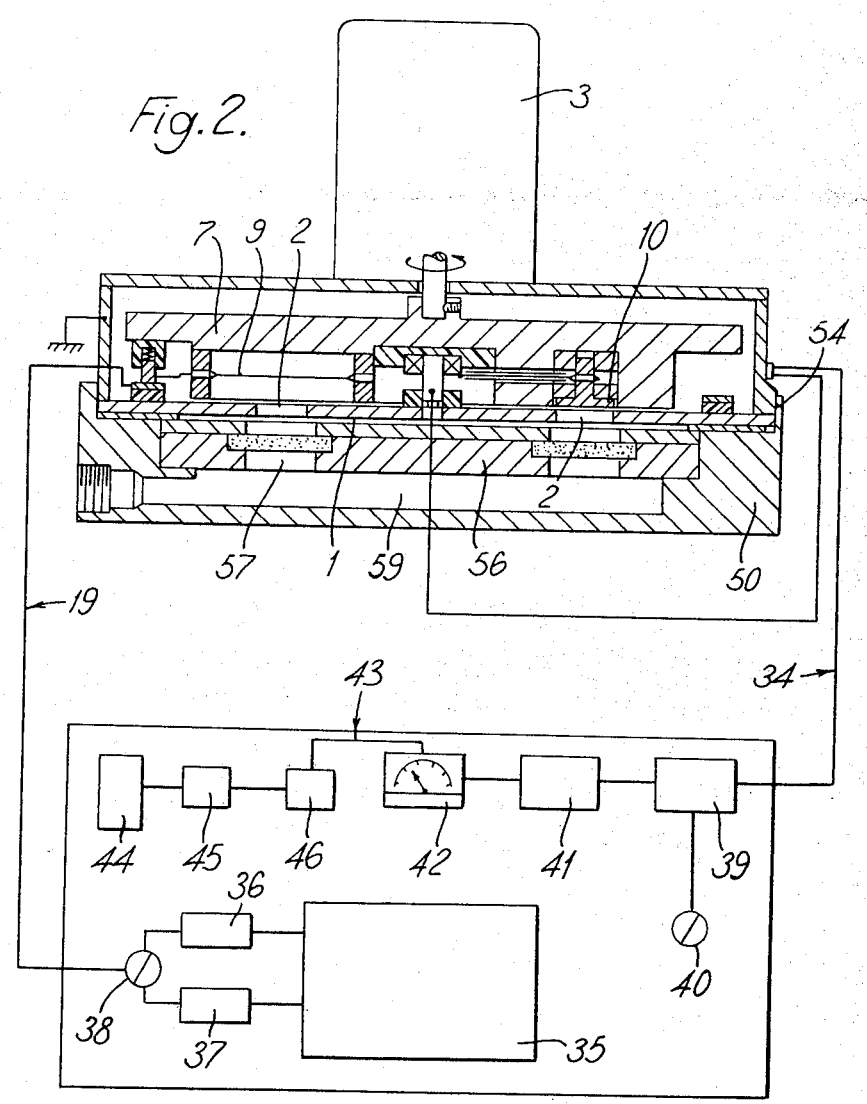
FIG. 2 is a diagrammatic view of the measuring head connected to a control box.

FIG. 2 shows the measuring head connected to a control box accommodating the high-tension generator and the measuring elements. A control box of this type permits full use to be made of the possibilities afforded by the measuring head. The charging electrode 9 is supplied by a conventional electrostatic generator 35 capable of supplying a continuous, effective high tension, the polarity of which may be selected by means of the high tension relays 36 and 37 and switch 38, connected by the connecting cable 19 to the contact track 17. Connected to the probe 10 by a cable 34, leading to an insulated cable, is an amplifier 39 provided with a gain control by potentiometer 40. The amplifier is connected to a circuit 41 for detecting the amplified signal and to a moving coil milliammeter 42. Advantageously, there may also be added to the milliammeter a timing circuit 43 comprising a generator 44 supplying electrical pulses at regular intervals, and one or more pulse counters, such as 45, each controlled by a relay 46, itself actuated on the passage of the milliammeter needle. There is thus determined automatically the time taken by the charge assumed by the material to fall to half, quarter or any other preselected fraction of its initial value (half-discharge time, three-quarters discharge time, etc.).

The control box may be connected to the mains or possibly it may be supplied by an independent source of voltage.

A second fixed plate 50 has its upper face 51 positioned opposite the first fixed plate 1 and a gasket 52 is preferably interposed between the block and the plate.

The plate 50 has a raised rim 53 and a lateral groove 54 corresponding to a lateral rib of the plate 1. These means make it possible to guide, center and hold the plate 1 in a fixed position relative to the plate 50.

A space 59 is provided inside the plate 50, and inside a part of this there can be placed two coaxial discs 55 and 56, having similar orifices 57 and 60 corresponding to the openings 2 of the plate 1. These orifices are again equidistant and distributed over a circle of diameter $d$. A porous element 58 is placed inside each of these orifices so that there are facing the openings 2, the same number of cavities 60, which can preferably be superposed over the said openings. The remainder of the space 59 extends between the plate 50 on the one hand and the discs 55 and 56 on the other hand, the space communicating with the exterior via a pipeline 61.

This pipeline connects the space 59 to means of any known type (not represented), such as a vacuum pump with its accessories, for sucking air through the porous elements 60.

The device according to the present application functions in the following way. Each cavity 60 above the porous element 58 is filled with the pulverulent or granular product to be investigated. The remainder of the apparatus is then placed on the plate 50 and thereafter, by means of the device for sucking air, air is sucked through the product to be investigated and the porous element. The suction effect is the stronger, the lower are the density and the particle size of the pulverulent product.

Measurements are then made, by connecting the apparatus to a high-tension generator and to a measuring apparatus, preferably to the previously described control box. The constant speed motor is started and rotates the rotor 7 and hence the charging electrode 9 and the measuring probe 10. A voltage is applied to the charging electrode after the desired polarity has been selected by means of the switch 38; the sheet is charged by corona effect.

When the measuring probe 10 is opposite an opening 2 allowing the charged specimens to appear, it acquires a charge by induction. This charge is substantially proportional to the potential to which the specimen is raised and to the capacitance of the probe relative to the specimen. During the rotation of the rotor 7, the area of the probe opposite the specimen varies, the capacitance of the whole varies and consequently so does the charge acquired by the probe.

The input circuit of the amplifier 39, to which the probe 10 is connected by the cable 34, is composed of resistances and consequently offers slight reactance; therefore the input signal received by the amplifier is proportional to the variation in time of the electric field to which the probe is subjected during its passage past the specimen opposite the openings. As a first approximation, the curve of variation of the signal is the derivative with respect to time of the charge acquired by the probe. This charge, first increasing and then decreasing, has the form of an alternation. Since the probe is periodically adjacent to two consecutive openings, two consecutive periods succeed each other without discontinuity and the variation of the potential of the probe appears in the form of an alternating periodical signal, which is easily amplified and detected. The amplitude of the signal is proportional to the potential to which the specimen is raised.

The charging tension is maintained for the necessary time (generally between 5 and 50 seconds) for the specimen to acquire a maximum charge; the gain control 40 of the amplifier 39 is operated to bring the needle of the milliammeter 42 to a predetermined position. The charging electrode is then disconnected from tension, which triggers the operation of the pulse generator 44 for producing on the pulse counters 45 the automatic display of the times of half-discharge, three-quarter discharge and generally preselected discharge fractions.

Before making measurements with the apparatus described, it may be necessary to calibrate it for verifying that it is functioning properly, for example after transport. To perform this calibration, it is possible for example to place under the plate 1 of the measuring head a conducting metal sheet insulated from the said plate and from earth. This plate is raised to a known potential supplied directly by the control box, the motor is started and the measuring circuit is connected up. The needle of the milliammeter 42 is then brought to a predetermined value (corresponding to the maximum of the scale) by means of the potentiometer 40 and the value indicated by the potentiometer index is read. The apparatus is in working order when the value as read corresponds to the value predetermined in the laboratory.

During a measurement "in situ," for example on paint covering a wall, the apparatus may be used in two distinct ways for determining the characteristics of the material alone (paint) or the material of its support. In the first case, the plate 1 of the measuring head is placed directly on the paint. In the second case, highly insulating feet (not shown) are placed between the plate 1 and the material.

It may sometimes be of interest to obtain the charging and discharging curve of the material examined. For this purpose, it is possible to connect the automatic discharge time display device to an oscilloscope or to a recorder (not shown).

For the exact determination of discharge times less than a second, the use of an oscilloscope or recorder is necessary.

The apparatus shown in FIG. 1 may be the object of various embodiment modifications. For example, the ball bearing 32 may be replaced by a roller or needle bearing. It is also possible to use corresponding ball, roller or needle thrust bearings. Preferably, these elements are sealed, particularly against dust.

The transmission of the measuring signal may also be effected by means of a rotating contact formed by a flexible blade wiping a shaft. The track 17 of the rotating contact supplying the charging electrode may be arranged on a diameter less than that of the recess 31. It may also be fixed either to the plate 1, support 4, or struts 5. It is also possible to change over the connections of the rotating contacts. Many other modifications will occur to the person versed in the art.

The function of the porous element is, on the one hand, to support and retain the pulverulent or granular product to be investigated, and on the other hand, to allow air to pass with a low pressure drop. The product to be investigated is thus held statically in the cavity 60, without the relative position of the elements of which it is composed being substantially changed at the surface, despite the air movements which take place during the measurements.

The electrostatic behavior of the product investigated during its discharge is thus not substantially changed. The device which forms the subject of the present application thus makes it possible to investigate the electrostatic behavior of pulverulent or granular products under the same conditions, and particularly with the same precision and the same reliability, as in the case of compact materials.

Grids, sieves, woven fabrics, non-woven fabrics and the like can be used as porous elements. Conducting materials, for example sintered metals, are preferably used. Of course, if desired, it is possible to superpose several porous elements of the same nature or of different nature.

The various parts such as the plate 50 of the discs 55 and 56 are advantageously made of conducting materials, for example metal. The plate 50 generally possesses an earthing terminal (not shown).

The apparatus makes it possible to investigate the electrostatic behavior of pulverulent or granular materials of very diverse nature, and especially plastics, the particle size of which is most frequently between 1 and 5,000 microns and more particularly between 20 and 500 microns.

It is known that pulverulent products can become charged with static electricity due to friction in handling installations (pneumatic transport) and storing installations, or in installations for effecting various treatments, for example drying. It becomes possible considerably to limit explosion risks in this type of installation if the electrostatic behavior of these products during their discharge is known, whether they are combustible or chemically inert when exposed to the atmosphere. The apparatus according to the present application makes it possible, especially, to carry out comparative experiments between different samples under conditions which are extremely similar to the actual use conditions.

The following example will illustrate the characteristics and the advantages of the present invention.

EXAMPLE

Apparatus as shown in the drawings is used. It has nine cavities of diameter 16 mm and depth 3 mm, distributed over a circle of diameter 80 mm. The bottom of each cavity is lined with a sintered stainless steel disc of thickness 2 mm and porosity 10 $\mu$.

The disc which carries the charging electrode and the measuring probe is driven at a speed of 1,500 revolutions/minute. It moves at a distance of 2.5 mm from the samples investigated. An absolute pressure of 10 mm of mercury is maintained under the porous elements.

A series of measurements are made under these conditions, the results of which are given in the following table:

| Experiment No. | Nature of the sample | State of the sample | Charge: potential acquired in volts | Discharge time in secs. | Percentage discharge reached |
|---|---|---|---|---|---|
| 1 | Polyvinyl chloride | Powder 200 $\mu$ | 330 | 900 | 7 |
| 2 | Hydroquinone | powder <50 $\mu$ | 370 | 900 | 45 |
| 3 | Polyethylene | Powder between 200 and 500 $\mu$ | 230 | 900 | 27 |
| 4 a | | Free powder | 250 | <4 | 50 |

-continued

| Experiment No. | Nature of the sample | State of the sample | Charge: potential acquired in volts | Discharge time in secs. | Percentage discharge reached |
|---|---|---|---|---|---|
| | Glyceryl guaiacol | 80% <125 μ | | | |
| 4 b | | Powder in pellet form | 250 | 4 | 50 |
| 5 a | | Free powder between 160 and 200 μ | 240 | 900 | 16 |
| | Acetylsalicylic acid | | | | |
| 5 b | | Powder in pellet form | 180 | 100 | 16 |

This table shows the time necessary ("Discharge time in seconds" column) for a particular sample to be discharged to the extent, expressed as a percentage, indicated in the right-hand column.

The first three experiments show differences in the electrostatic behavior, during discharge, of samples of various natures.

The other experiments clearly show that the electrostatic behavior, during discharge, of a powder of a particular nature is very different and even difficult to predict, depending on whether it is in the free state or in pellet form.

I claim:

1. Apparatus for measuring the electrostatic properties of materials, said apparatus comprising, in combination:
   a. a first fixed plate;
   b. a rotor mounted to rotate about an axis perpendicular to said fixed plate;
   c. means defining openings in said fixed plate, the openings lying along the circumference of a circle, the center of said circle lying on said axis of said rotor;
   d. an electrode and a probe fixed to said rotor and spaced apart from one another and positioned whereby both the electrode and the probe separately overlie each of said openings in turn when the rotor rotates;
   e. means for charging said electrode;
   f. means for detecting the charge on said probe, thereby detecting the charge on said materials;
   g. a second fixed plate having means to hold it against said first fixed plate;
   h. means defining material containing cavities in said second fixed plate at locations overlying the openings in said first fixed plate;
   i. at least one porous element at the bottom of each said cavity; and
   j. means for sucking air at the bottom of the said cavities through said porous elements thereby holding said materials contained in said cavities against displacement.

2. Apparatus as claimed in claim 1, and further comprising a motor carried by said first plate for rotating said rotor at a constant speed.

3. Apparatus as claimed in claim 1, wherein said porous element is made of sintered metal.

* * * * *